US006541664B1

(12) United States Patent
Jachow et al.

(10) Patent No.: US 6,541,664 B1
(45) Date of Patent: Apr. 1, 2003

(54) METHOD OF HETEROGENEOUS CATALYZED VAPOR-PHASE OXIDATION OF PROPANE TO ACROLEIN AND/OR ACRYLIC ACID

(75) Inventors: Harald Jachow, Bensheim; Andreas Tenten, Maikammer; Signe Unverricht; Heiko Arnold, both of Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/509,553

(22) PCT Filed: Oct. 5, 1998

(86) PCT No.: PCT/EP98/06301

§ 371 (c)(1),
(2), (4) Date: Apr. 13, 2000

(87) PCT Pub. No.: WO99/20590

PCT Pub. Date:Apr. 29, 1999

(30) Foreign Application Priority Data

| Oct. 21, 1997 | (DE) | 197 46 210 |
| Oct. 23, 1997 | (DE) | 197 46 667 |
| Dec. 4, 1997 | (DE) | 197 53 817 |
| Nov. 19, 1997 | (DE) | 197 51 046 |
| Feb. 20, 1998 | (DE) | 198 07 079 |

(51) Int. Cl.[7] ........................................... C07C 51/215
(52) U.S. Cl. .................. 562/549; 562/542; 562/577; 568/470; 568/475
(58) Field of Search ................... 562/542, 549, 562/577; 568/470, 475

(56) References Cited

U.S. PATENT DOCUMENTS

| 2,625,519 A | | 1/1953 | Hartig | 252/432 |
| 4,066,704 A | * | 1/1978 | Harris et al. | 260/604 |
| 5,191,116 A | | 3/1993 | Yamamatsu et al. | 562/449 |
| 5,198,580 A | | 3/1993 | Bartek et al. | 562/542 |
| 5,364,825 A | | 11/1994 | Neumann et al. | 502/311 |

FOREIGN PATENT DOCUMENTS

| CN | 1105352 | 11/1994 |
| DE | 195 30 454 | 2/1997 |
| DE | 196 22 331 | 12/1997 |
| EP | 0 117 146 | 8/1984 |
| EP | 0 575 897 | 12/1993 |
| EP | 0 608 838 | 8/1994 |
| FR | 2 693 384 | 1/1994 |
| FR | 2 756 499 | 6/1998 |
| GB | 1 340 891 | 12/1973 |
| GB | 1 398 385 | 6/1975 |
| JP | 2-083348 | 3/1990 |
| WO | WO 97/36849 | 10/1997 |

OTHER PUBLICATIONS

Y. Moro–Oka[a], et al., "Selective Oxidation and Ammoxidation of Propane to Form Acrolein and Acrylonitrile", Proceedings of the 10th International Congress on Catalysis, Jul. 19–24, 1992, pp. 1982–1986.

M. Baerns[b], et al., "Catalytic Partial Oxidation of Propane to Acrolein", Catalysis Today, vol. 33, pp. 85–96, 1997.

Young Seek Yoon[a], "Selective Conversion of Propane to Propene by the Catalytic Oxidative Dehydrogenation over Cobalt and Magnesium Molybdates", Topics in Catalysis, vol. 3, pp. 265–275, 1996.

David L. Stern, et al., "Propane Oxydehydrogenation over Molybdate–Based Catalysts", Journal of Catalysis, Article No. CA971568, vol. 167, pp. 550–559, 1997.

J. Barrault[a], et al., "Selective Oxidation of Propane into Oxygenated Compounds over Promoted Nickel–Molybdenum Catalysts", 3rd World Congress on Oxidation Catalysis, pp. 375–382, 1997.

* cited by examiner

*Primary Examiner*—Paul J. Killos
*Assistant Examiner*—Robert W. Deemie
(74) *Attorney, Agent, or Firm*—Oblon, Spivak, McClelland, Maier & Neustadt, P.C.

(57) ABSTRACT

In a process for heterogeneously catalyzed gas-phase oxidation, a reaction gas starting mixture comprising propane, molecular oxygen and, if desired, inert gas is passed at from 300 to 500° C. over a fixed-bed catalyst.

17 Claims, No Drawings

METHOD OF HETEROGENEOUS CATALYZED VAPOR-PHASE OXIDATION OF PROPANE TO ACROLEIN AND/OR ACRYLIC ACID

BACKGROUND OF THE INVENTION

1. Field of the Invention

The present invention relates to a process for the heterogeneously catalyzed gas-phase oxidation of propane to acrolein and/or acrylic acid, in which a reaction gas starting mixture comprising propane, molecular oxygen and, if desired, inert gas is passed at from 300 to 500° C. over a fixed-bed catalyst.

2. Discussion of the Background

Acrolein and acrylic acid are important intermediates which are employed, for example, for producing active compounds and polymers.

At present, by far the most widely employed process for the industrial preparation of acrolein and/or acrylic acid is the gas-phase catalytic oxidation of propene (for example EP-A 575897), with the propene being mostly produced as a by-product of ethylene production by steam cracking of naphtha. Since the other application areas for propene, e.g. the production of polypropylene, continue to expand, it would be advantageous to have an industrially usable, competitive process for preparing acrolein and/or acrylic acid which uses as raw material not propene but propane which, for example, occurs naturally in large amounts as a constituent of natural gas.

EP-A 117146 proposes preparing acrylic acid from propane by converting propane into a propylene-containing product stream by means of heterogeneous catalytic dehydrogenation in the absence of molecular oxygen in a first stage and, in subsequent oxidation stages, passing this product stream together with molecular oxygen over suitable oxidation catalysts so as to oxidize the propene present therein to acrolein and/or acrylic acid.

A disadvantage of this procedure is that it necessarily requires a plurality of reaction stages, with the individual reaction stages having to be carried out under different reaction conditions.

Furthermore, the abovementioned procedure has the disadvantage that the catalyst required for the nonoxidative dehydrogenation of the propane is relatively quickly deactivated as a result of carbon deposits and has to be regenerated. Since the dehydrogenation product mixture also contains hydrogen, CN-A 1105352 casts doubt on the possibility of passing the dehydrogenation product mixture on directly to a subsequent oxidation stage.

Both CN-A 1105352 and Y. Moro-oka in Proceedings of the 10th International Congress on Catalysis, Jul. 19–24, 1992, Budapest, Hungary, 1993, Elsevier Science Publishers B. V., pp. 1982 to 1986, recommend first converting propane partially into propene in a homogeneous oxidative dehydrogenation and converting this propene, without separating it off beforehand, into acrolein and/or acrylic acid in subsequent heterogeneously catalyzed oxidation stages. Disadvantages of this procedure are, on the one hand, that carbon is also formed in a homogeneous oxidative dehydrogenation of propane to propene and, on the other hand, that the selectivity of the formation of the desired product (acrolein and/or acrylic acid) is not satisfactory in such a procedure. Thus, in the examples in CN-A 1105352, the selectivity of propene formation achieved by homogeneous oxidative dehydrogenation is only $\leq 40\%$ by volume and Moro-oka is also restricted to selectivities of acrolein formation of 64 mol %, based on propane reacted.

It has also been proposed that a heterogeneously catalyzed oxidative dehydrogenation of propane (which is not necessarily accompanied by carbon formation) be coupled with a subsequent heterogeneously catalyzed oxidation of the propene thus produced to give acrolein and/or acrylic acid (e.g. 210th ACS National Meeting, Chicago, Aug. 20–24, 1995 or WO 97/36849). However, further details regarding the type and manner of the coupling (in general, both reaction steps require reaction conditions which cannot be reconciled) were not given. CN-A 1105352 even advises decidedly against such a coupling, since, at reasonable propane conversions, achievable selectivities of propene formation in a heterogeneously catalyzed oxidative dehydrogenation do not exceed those in a homogeneous oxidative dehydrogenation.

Topics in Catalysis 3(1996), pp. 265–275, reports the heterogeneously catalyzed oxidative dehydrogenation of propane to propene over cobalt molybdate and magnesium molybdate. A disadvantage of the procedure of the abovementioned reference is that it is, presumably to ensure a satisfactory selectivity of propene formation, carried out in high dilution, i.e. the reaction gas starting mixture comprising propane and molecular oxygen further comprises up to 75% by volume of molecular nitrogen (inert gas). Such a high proportion of inert gas does not encourage coupling with a subsequent propene oxidation, since it reduces the space-time yields of acrolein and/or acrylic acid achievable in a single pass. Furthermore, such a proportion of nitrogen makes it more difficult to recirculate unreacted propane and/or propene after having separated off acrolein and/acrylic acid, should this be intended subsequent to the propene oxidation.

Journal of Catalysis 167 (1997), 550–559 likewise reports the heterogeneously catalyzed oxidative dehydrogenation of propane to propene or molybdates. A disadvantage of the procedure in this reference is that it likewise recommends the use of a reaction gas starting mixture whose proportion of molecular nitrogen is 70% by volume. Furthermore, the abovementioned reference proposes a dehydrogenation temperature of 560° C. Such a high dehydrogenation temperature likewise does not suggest coupling to a downstream heterogeneously catalyzed propene oxidation, since it damages the multimetal oxide compositions customarily used for an oxidative conversion of propene into acrolein and/or acrylic acid.

Journal of Catalysis 167 (1997), 560–569 likewise recommends a dehydrogenation temperature of 560° C. for a heterogeneously catalyzed oxidative dehydrogenation. Similarly, DE-A 19530454 similarly recommends temperatures above 500° C. for a heterogeneously catalyzed oxidative dehydrogenation of propane to give propene.

Furthermore, experiments on a heterogeneously catalyzed direct oxidation of propane to acrolein and/or acrylic acid are reported in the literature (e.g. Proceedings, 210th ACS National Meeting, Chicago, Aug. 20–24, 1995, FR-A 2693384 and 3rd World Congress on Oxidation Catalysis, R. K. Grasselli, S. T. Oyama, A. M. Gaffney and J. E. Lyons (Editors), 1997 Elsevier Science B.V., pp. 375–382), although in these studies, too, either the reported selectivity of the acrolein and/or acrylic acid formation and/or the reported yield of acrolein and/or acrylic acid on a single pass are not satisfactory.

EP-B 608838 likewise relates to the heterogeneously catalyzed direct oxidation of propane to acrylic acid.

However, a disadvantage of the method disclosed in EP-B 608838 is that the selectivities of the acrylic acid formation reported by way of example in this document cannot be reproduced. Thus, our attempts to repeat the work gave a vanishing selectivity for acrylic acid formation. Instead, formation of acrolein was found when repeating these examples, but the selectivity for the acrolein formation was only ≦30 mol %.

SUMMARY OF THE INVENTION

It is an object of the present invention to provide a process for the heterogeneously catalyzed gas-phase oxidation of propane to acrolein and/or acrylic acid, in which a reaction gas starting mixture comprising propane, molecular oxygen and, if desired, inert gas is passed at from 300 to 500° C. over a fixed-bed catalyst, which process does not have the disadvantages of the methods described and/or recommended in the prior art.

DETAILED DESCRIPTION OF THE INVENTION

We have found that this object is achieved by a process for the heterogeneously catalyzed gas-phase oxidation of propane to acrolein and/or acrylic acid, in which a reaction gas starting mixture comprising propane, molecular oxygen and, if desired, inert gas is passed at from 300 to 500° C. over a fixed-bed catalyst which comprises two catalyst beds A and B arranged spatially in succession, with the proviso that the active composition of bed A is at least one multimetal oxide of the formula I $$M^1_a Mo_{1-b} M^2_b O_x$$

where $M^1$=Co, Ni, Mg, Zn, Mn and/or Cu, preferably Co, Ni and/or Mg, particularly preferably Co and/or Ni, $M^2$=W, V, Te, Nb, P, Cr, Fe, Sb, Ce, Sn and/or La, preferably Sn, W, P, Sb and/or Cr, particularly preferably W, Sn and/or Sb, a=0.5–1,5, preferably 0.7–1.2, particularly preferably 0.9–1.0, b=0–0.5, preferably >0–0.5 and particularly preferably 0.01–0.3, and x=a number which is determined by the valence and amount of the elements different from oxygen in I, and the active composition of bed B is at least one multimetal oxide of the formula II $$Bi_a, Mo_b, X^1_c, X^2_d, X^3_e, X^4_f, X^5_g, X^6_h, O_x, \qquad (II),$$

where $X^1$=W, V and/or Te, preferably W and/or V $X^2$=alkaline earth metal, Co, Ni, Zn, Mn, Cu, Cd, Sn and/or Hg, preferably Co, Ni, Zn and/or Cu, particularly preferably Co, Ni and/or Zn, $X^3$=Fe, Cr and/or Ce, preferably Fe and/or Cr, $X^4$=P, As, Sb and/or B, preferably P and/or Sb, $X^5$=alkali metal, Tl and/or Sn, preferably K and/or Na, $X^6$=rare earth metal, Ti, Zr, Nb, Ta, Re, Ru, Rh, Ag, Au, Al, Ga, In, Si, Ge, Th and/or U, preferably Si, Zr, Al, Ag, Nb and/or Ti, a'=0.01–8, preferably 0.3–4 and particularly preferably 0.5–2, b'=0.1–30, preferably 0.5 to 15 and particularly preferably 10–13, c'=0–20, preferably 0.1 to 10 and particularly preferably 0.5–3, d'=0–20, preferably 2–15 and particularly preferably 3–10, e'=0–20, preferably 0.5–10 and particularly preferably 1–7, f'=0–6, preferably 0–1, g'=0–4, preferably 0.01–1, h'=0–15, preferably 1–15 and x'=a number which is determined by the valence and amount of the elements different from oxygen in II, wherein the reaction gas starting mixture comprises ≧50% by volume of propane, ≧15% by volume of $O_2$ and from 0 to 35% by volume of inert gas and flows through the catalyst beds A and B in the order first A, then B.

Preferred multimetal oxides I are accordingly those of the formula I'

$$[Co, Ni \text{ a./o. } Mg]_a Mo_{1-b} [Sn, W, P, Sb \text{ a./o. } Cr]_b O_x \qquad (I'),$$

where a=0.5–1.5, preferably 0.7–1.2, particularly preferably 0.9–1.0, b=0–0.5, preferably >0–0.5 and particularly preferably 0.01–0.3, and x is a number which is determined by the valence and amount of the elements different from oxygen in I'.

Particularly preferred multimetal oxides I are those of the formula I"

$$[Co \text{ a./o. } Ni]_a Mo_{1+b} [W, Sn \text{ a./o. } Sb]_b O_x \qquad (I''),$$

where a, b and x are as defined above.

Preferred multimetal oxides II are those of the formula II'

$$Bi_a, Mo_b, W_c, [Co, Nia./o.Zn]_d, Fe_e, [Pa./o.Sb]_f, [Ka./o.Na]_g, X^6_h, O_x, \qquad (II'),$$

where $X^6$ and the stoichiometric coefficients are as defined for formula II.

Particularly preferred multimetal oxides II' are those in which $X^6$=Si, Zr, Al, Nb, Ag and/or Ti, among which preference is in turn given to those in which $X^6$=Si.

It is also advantageous for e' to be 0.5–10, particularly when $X^6$=Si.

The above applies particularly when the multimetal oxide compositions II' as described in EP-B 575897 are being prepared.

Particularly advantageous catalyst bed pairs A, B are the combinations I', II' and I", II'. This applies particularly when $X^6$=Si and e'=0.5–10.

In the process of the present invention, the reaction gas starting mixture is advantageously passed over the fixed-bed catalyst comprising catalyst beds A and B at from 325 to 480 or 450° C., preferably from 350 to 420° C. and particularly preferably from 350 to 400° C. Normally, the catalyst beds A, B have identical temperatures.

If the catalyst bed pair A, B used is a combination I', II' or I", II', the reaction temperature in both beds is advantageously from 350 to 420° C., frequently from 350 to 400° C.

Furthermore, the reaction gas starting mixture advantageously comprises ≦30% by volume, preferably ≦20% by volume and particularly preferably ≦10% by volume or ≦5% by volume, of inert gas. Of course, the reaction gas starting mixture can also contain no inert gas. In the present context, inert gases are gases which are reacted to an extent of ≦5 mol % on passing through the fixed-bed catalyst to be used according to the present invention. Possible inert gases are, for example, $H_2O$, $CO_2$, CO, $N_2$ and/or noble gases.

Moreover, the reaction gas starting mixture advantageously comprises ≧60% by volume or ≧70% by volume or ≧80% by volume of propane. The propane content of the reaction gas starting mixture to be used according to the present invention is generally ≦85% by volume, frequently ≦83 or ≦82 or ≦81 or ≦80% by volume. The amount of molecular oxygen present in the reaction gas starting mixture can be up to 35% by volume in the process of the present invention. It is advantageously at least 20% by volume or at least 25% by volume. Reaction gas starting mixtures which are useful according to the present invention comprise ≧65% by volume and ≦85% by volume of propane plus ≧15% by volume and ≦35% by volume of molecular oxygen. According to the invention, it is advantageous (in respect of selectivity and conversion) for the molar ratio of propane to molecular oxygen in the reaction gas starting mixture to be <5:1, preferably ≦4.75:1, better ≦4.5:1 and particularly preferably ≦4:1. As a rule, the abovementioned ratio will be ≧1:1 or ≧2:1.

In principle, active compositions I which are suitable according to the present invention can be readily prepared by making up an intimate, preferably finely divided dry mixture of suitable sources of their elemental constituents which has a composition corresponding to their stoichiometry and calcining this mixture at from 450 to 1000° C. The calcination can be carried out either under inert gas or in an oxidizing atmosphere such as air (mixture of inert gas and oxygen) or else in a reducing atmosphere (e.g. mixture of inert gas, oxygen and $NH_3$, CO and/or $H_2$). The calcination time can be from a few minutes to a few hours and usually decreases with increasing temperature. Suitable sources of the elemental constituents of the active multimetal oxide compositions I are compounds which are already oxides and/or compounds which can be converted into oxides by heating, at least in the presence of oxygen.

Apart from the oxides, suitable starting compounds are, in particular, halides, nitrates, formates, oxalates, citrates, acetates, carbonates, amine complexes, ammonium salts and/or hydroxides (compounds such as $NH_4OH$, $(NH_4)_2CO3$, $NH_4NO_3$, $NH_4CHO_2$, $CH_3COOH$, $NH_4CH_3CO_2$ and/or ammonium oxalate, which dissociate and/or can be decomposed at the latest during the subsequent calcination to form compounds which are all given off in gaseous form, can be additionally incorporated into the intimate dry mixture). The intimate mixing of the starting compounds to produce multimetal oxide compositions I can be carried out in dry or wet form. If it is carried out in dry form, the starting compounds are advantageously used as finely divided powders and are subjected to calcination after mixing and, if desired, compaction. However, the intimate mixing is preferably carried out in wet form. Here, the starting compounds are usually mixed with one another in the form of an aqueous solution and/or suspension. Particularly intimate dry mixtures are obtained in the mixing process described if all the sources of the elemental constituents used are present in dissolved form. The solvent used is preferably water. The resulting aqueous composition is subsequently dried, with the drying process preferably being carried out by spray drying of the aqueous mixture at outlet temperatures of from 100 to 150° C. Particularly suitable starting compounds of Mo, V, W and Nb are their oxo compounds (molybdates, vanadates, tungstates and niobates) or the acids derived from these. This applies particularly to the corresponding ammonium compounds (ammonium molybdate, ammonium vanadate, ammonium tungstate).

In the process of the present invention, the multimetal oxide compositions I can be used either in powder form or after shaping to give particular catalyst geometries; shaping can be carried out before or after the subsequent calcination.

For example, unsupported catalysts can be produced from the powder form of the active composition or its uncalcined precursor composition by compaction to give the desired catalyst geometry (e.g. by tableting or extrusion). If desired, auxiliaries such as graphite or stearic acid as lubricants and/or shaping aids and reinforcing materials such as microfibers of glass, asbestos, silicon carbide or potassium titanate can be added. Suitable unsupported catalyst geometries are, for example, solid cylinders or hollow cylinders having an external diameter and a length of from 2 to 10 mm. In the case of the hollow cylinders, a wall thickness of from 1 to 3 mm is advantageous. Of course, the unsupported catalyst can also have a spherical geometry, in which case the sphere diameter can be from 2 to 10 mm.

Of course, the shaping of the pulverulent active composition or its pulverulent but not yet calcined precursor composition can also be achieved by application to preshaped inert catalyst supports. The coating of the support bodies to produce the coated catalysts is generally carried out in a suitable rotatable container, as is known, for example, from DE-A 2909671 or EP-A 293859. To coat the support bodies, it is advantageous to moisten the powder composition to be applied and to dry it again after application, e.g. by means of hot air. The thickness of the layer of powder composition applied to the support body is advantageously selected so as to be in the range from 50 to 500 μm, preferably in the range from 150 to 250 μm.

Support materials which can be used here are customary porous or nonporous aluminum oxides, silicon dioxide, thorium dioxide, zirconium dioxide, silicon carbide or silicates such as magnesium silicate or aluminum silicate. The support bodies can have regular or irregular shapes, with preference being given to support bodies having a regular shape and a distinct surface roughness, e.g. spheres or hollow cylinders. Essentially nonporous, spherical steatite supports which have a rough surface and a diameter of from 1 to 8 mm, preferably from 4 to 5 mm, are useful.

As regards the preparation of the multimetal oxide compositions II, what has been said for the multimetal oxide compositions I applies. However, the calcination temperature employed is generally from 350 to 650° C. Particularly preferred multimetal oxide compositions II are the multimetal oxide compositions I disclosed in EP-B 575897, particularly their preferred variants. In these, multimetal oxides are first preformed from portions of the elemental constituents and are used as element source in the further course of the preparation.

The process of the present invention is advantageously carried out in multitube reactors as are described, for example, in EP-A 700893 and EP-A 700714. The fixed-bed catalyst to be used according to the present invention is located in the metal tubes (in general of stainless steel) and a heat transfer medium, in general a salt melt, is passed around the metal tubes. In the simplest case, the two catalyst beds A and B to be used according to the present invention are arranged in direct succession in each reaction tube. The ratio of the bed volumes of the two catalyst beds A and B is, according to the present invention, advantageously from 1:10 to 10:1, preferably from 1:5 to 5:1 and particularly preferably from 1:2 to 2:1, frequently 1:1. The reaction pressure is generally ≧0.5 bar. Normally, the reaction pressure will not exceed 100 bar, i.e. it will be from ≧0.5 to 100 bar. It is frequently advantageous for the reaction pressure to be from >1 to 50 bar or from >1 to bar. The reaction pressure is preferably ≧1.25 or ≧1.5 bar or ≧1.75 or ≧2 bar. Frequently, the upper limit of 10 or 20 bar is not exceeded here. Of course, the reaction pressure can also be 1 bar (the above statements regarding the reaction pressure apply quite generally to the process of the present invention). Furthermore, the space velocity is advantageously selected such that the residence time of the reaction gas mixture over the two catalyst beds A and B is from 0.5 to 20 sec, preferably from 1 to 10 sec, particularly preferably from 1 to 4 sec and frequently from 3 sec. Propane and/or propene present in the product mixture from the process of the present invention can be separated off and returned to the gas-phase oxidation according to the present invention. Furthermore, the process of the present invention can be followed by a further heterogeneously catalyzed oxidation stage as is known for the heterogeneously catalyzed gas-phase oxidation of acrolein to acrylic acid, into which the product mixture of the process of the present invention, if desired with the addition of further molecular oxygen, is conveyed. At the end of this, unreacted propane, propene and/or acrolein can again be separated off and returned to the gas-phase oxidation. The acrolein and/or acrylic acid formed can be separated from the product gas mixtures in a manner known per se. In general, the propane conversion achieved using the process of the present invention is $\geq 5$ mol %, or $\geq 7.5$ mol %. However, propane conversions of $\geq 20$ mol % are not normally achieved. The process of the present invention is particularly suitable for continuous operation. If necessary, additional molecular oxygen can be injected at the level of the catalyst bed B. Conversion, selectivity and residence time referred to in this document are, unless indicated otherwise, defined as follows:

mm was separated by sieving as the catalytically active multimetal oxide composition I of the stoichiometry $Mo_1Co_{0.95}O_x$.

b) Preparation of a Multimetal Oxide Composition II

1. Preparation of a Starting Composition 50 kg of a solution of $Bi(NO_3)_3$ in aqueous nitric acid (11% by weight of Bi, 6.4% by weight of $HNO_3$, in each case based on the solution) was admixed with 13.7 kg of ammonium paratungstate (89% by weight of $WO_3$) and stirred for 1 hour at 50° C. The suspension obtained was spray-dried and calcined for 2 hours at 750° C. The resulting preformed calcined mixed oxide was milled and the particle size fraction 1 $\mu m \leq d \leq 5$ $\mu m$ (d=particle diameter) was separated out. This particle size fraction was subsequently mixed with 1% of its weight of finely divided $SiO_2$ (number average particle diameter: 28 nm).

2. Preparation of a Starting Composition 2

48.9 kg of $Fe(NO_3)_3$ were dissolved in 104.6 kg of cobalt nitrate solution (12.5% by weight of Co, based on the solution). The resulting solution was added to a solution of 85.5 kg of ammonium heptamolybdate (81.5% by weight of $MoO_3$) in 240 l of water. The resulting mixture was admixed with 7.8 kg of an aqueous mixture containing 20% of its weight of colloidal $SiO_2$, and with 377 g of an aqueous solution containing 48% by weight of KOH. This mixture was subsequently stirred for 3 hours and the resulting aqueous suspension was spray-dried to give the starting composition 2.

$$\text{Conversion of propane (mol \%)} = \frac{\text{Number of moles of propane reacted}}{\text{Number of moles of propane fed in}} \times 100$$

Selectivity S of acrolein and/or = 
acrylic acid formation (mol %)

$$\frac{\text{Number of moles of propane converted into acrolein and/or acrlic acid}}{\text{Number of moles of propane reacted}} \times 100$$

Residence time (sec) =

$$\frac{\text{free volume of the reactor (1) in the zone where the catalyst is located}}{\text{amount of reaction gas starting mixture passed through}} \times 3600$$

EXAMPLES

Example 1 a) Preparation of a Multimetal Oxide Composition I 292.4 g of ammonium heptamolybdate (81.5% by weight of $MoO_3$) were dissolved at 80° C. in 1.2 kg of water and the resulting solution was admixed with 742.4 g of aqueous cobalt nitrate solution (12.5% by weight of Co, based on the solution). The solution formed was evaporated while stirring on a water bath at 100° C. until a paste-like mass had been formed. This was subsequently dried for 16 hours at 110° C. in a drying oven and subsequently calcined in a stream of air in a muffle furnace (60 l internal volume, air throughput: 500 l/h), as follows: The temperature was first increased from room temperature (25° C.) to 300° C. at a heating rate of 120° C./h. The temperature of 300° C. was subsequently held for 3 hours and the calcination temperature was then increased from 300 to 550° C. at a heating rate of 125° C./h. This temperature was subsequently held for 6 hours. The resulting multimetal oxide was comminuted and the particle size fraction having a particle diameter of from 0.6 to 1.2

3. Preparation of the Multimetal Oxide II

The starting composition 1 was mixed with the starting composition 2 in the amount required for a multimetal oxide II of the stoichiometry

pressed to form hollow cylinders having a length of 3 mm, an external diameter of 5 mm and a wall thickness of 1.5 mm and subsequently calcined as follows. The calcination was carried out in a stream of air in a muffle furnace (60 l internal volume, 1 l/h of air per gram of catalyst precursor composition). The temperature was first increased from room temperature (25° C.) to 190% at a heating rate of 180° C./h. This temperature was held for 1 hour and then increased to 220° C. at a heating rate of 60° C./h. The 220° C. was again held for 2 hours before being increased to 260° C. at a heating rate of 60° C./h. The 260° C. was subsequently held for 1 hour. The mixture was then first cooled to room temperature, thus essentially concluding the decomposition phase, and then heated to 465° C. at a heating rate of 180° C./h and this calcination temperature was held for 4 hours.

200 g of the resulting active composition were comminuted and the particle size fraction from 0.6 to 1.2 mm was sieved out as active multimetal oxide composition II.

c) Gas-phase Catalytic Oxidation of Propane

A reaction tube (V2A steel; 2.5 cm wall thickness; 8.5 mm internal diameter; electrically heated) having a length of 1.4 m was charged, from the bottom upward on a catalyst base (7 cm length), first to a length of 13 cm with quartz granules (number average particle diameter from 1 to 2 mm) and subsequently to a length of 42.5 cm with the active multimetal oxide composition II and then to a length of 42.5 cm with the active multimetal oxide composition I, before the charge was completed to a length of 13 cm with quartz granules (number average particle diameter from 1 to 2 mm).

The reaction tube charged as described above was heated to 430° C. over its entire length and then supplied, from the top downward, with 56 standard l/h of a reaction gas starting mixture consisting of 80% by volume of propane and 20% by volume of oxygen.

In a single pass, a product gas mixture having the following characteristics was obtained:

Propane conversion: 10 mol %
Selectivity of acrolein formation: 59 mol %
Selectivity of acrylic acid formation: 14 mol %
Selectivity of propene formation: 3 mol %

Example 2 a) Preparation of a Multimetal Oxide Composition I

The preparation of the multimetal oxide composition I was carried out as in Example 1a), but the final calcination temperature was 560° C. instead of 550° C.

b) Preparation of a Multimetal Oxide Composition II

The preparation of the multimetal oxide composition II was carried out as in Example 1b).

c) Gas-phase Catalytic Oxidation of Propane

A reaction tube (V2A steel; 2.5 cm wall thickness; 8.5 mm internal diameter; electrically heated) having a length of 1.4 m was charged, from the bottom upward on a catalyst base (7 cm length), first to a length of 18 cm with quartz granules (number average particle diameter from 1 to 2 mm) and subsequently to a length of 42.5 cm with the active multimetal oxide composition II and then to a length of 42.5 cm with the active multimetal oxide composition I, before the charge was completed to a length of 30 cm with quartz granules (number average particle diameter from 1 to 2 mm).

The reaction tube charged as described above was heated to 415° C. over its entire length and then supplied, from the top downward, with 56 standard l/h of a reaction gas starting mixture consisting of 80% by volume of propane and 20% by volume of oxygen. The pressure at the inlet of the reaction tube was 1.68 bar (absolute). The pressure drop along the reaction tube was 0.27 bar.

In a single pass, a product gas mixture having the following characteristics was obtained:

propane conversion: 11.5 mol %
selectivity of acrolein formation: 66 mol %
selectivity of acrylic acid formation: 10 mol %
selectivity of propane formation: 2 mol %

Example 3 a) Preparation of a Multimetal Oxide Composition I 877.2 g of ammonium heptamolybdate (81.5% by weight of $MoO_3$) were dissolved at 45° C. in 3.6 kg of water and the resulting solution was admixed with 2227.2 g of aqueous cobalt nitrate solution (12.5% by weight of Co based on the solution).

The resulting clear, red solution was spray-dried in a spray dryer from Niro (A/S Niro Atomizer transportable Minor) at an inlet temperature of 330–340° C. and an outlet temperature of 110° C. 450 g of the spray-dried powder obtained were kneaded (1 l sigma-blade kneader from Werner & Pfleiderer) with 75 ml of $H_2O$ for 40 minutes and dried at 110° C. for 16 hours in a convection drying oven. The dried powder was subsequently calcined in a rotating (15 revolutions/min) round-bottomed quartz flask through which air flowed (internal volume: 2 l, air throughput: constant 250 l/h) as follows (tilting oven heating):

The temperature was first raised from room temperature (25° C.) to 225° C. at a heating rate of 180° C./h. The temperature of 225° C. was subsequently held for 0.5 hour and the calcination temperature as then increased from 225° C. to 300° C. at a heating rate of 60° C./h. This temperature was subsequently held for 3 hours. The calcination temperature was then increased from 300 to 550° C. at a heating rate of 125° C./h. This temperature was subsequently held for 6 hours.

The multimetal oxide thus obtained was comminuted and the particle size fraction having a particle diameter of from 0.6 to 1.2 mm was separated out by sieving as the catalytically active multimetal oxide composition I of the stoichiometry $Mo_1Co_{0.95}O_x$.

b) Preparation of a Multimetal Oxide Composition II

The preparation of the multimetal oxide composition II was carried out as in Example Ib).

c) Gas-phase Catalytic Oxidation of Propane

A reaction tube (V2A steel; 2.5 cm wall thickness; 8.5 mm internal diameter; electrically heated) having a length of 1.4 m was charged, from the bottom upward on a catalyst base (7 cm length), first to a length of 18 cm with quartz granules (number average particle diameter from 1 to 2 mm) and subsequently to a length of 42.5 cm with the active multimetal oxide composition II and then to a length of 42.5 cm with the active multimetal oxide composition I, before the charge was completed to a length of 30 cm with quartz granules (number average particle diameter from 1 to 2 mm).

The reaction tube charged as described above was heated to 390° C. over its entire length and then supplied, from the top downward, with 84 standard l/h of a reaction gas starting mixture consisting of 80% by volume of propane and 20% by volume of oxygen. The pressure at the inlet of the reaction tube was 2.7 bar (absolute). The pressure drop along the reaction tube was 0.35 bar.

In a single pass, a product gas mixture having the following characteristics was obtained:

propane conversion: 9.0 mol %
selectivity of acrolein formation: 69 mol %
selectivity of acrylic acid formation: 10 mol %
selectivity of propane formation: 1 mol %

Example 4 a) Preparation of a multimetal oxide composition I 929.3 g of ammonium heptanemolybdate (81.5% by weight of $MoO_3$) were dissolved at 45° C. in 1.5 kg of water. 80.8 g of ammonium paratungstate (89.04% by weight of $WO_3$) were dissolved separately at 95–98° C. in 1.5 kg of water and subsequently cooled to 45° C. The two solutions were combined at 45° C. and admixed with an aqueous cobalt nitrate solution (12.5% by weight of Co based on the solution) which was likewise at 45° C.

The resulting clear, red solution was spray-dried in a spray dryer from Niro (A/S Niro Atomizer transportable Minor) at an inlet temperature of 320° C. and an outlet temperature of 110° C. 450 g of the spray-dried powder obtained were kneaded (1 l sigma-blade kneader from Werner & Pfleiderer) with 85 ml of $H_2O$ for 40 minutes and dried at 110° C. for 16 hours in a convection drying oven. The dried composition was subsequently calcined in a stream of air in a muffle furnace (internal volume: 60 l, air throughput: constant 500 l/h) as follows.

The temperature was first raised from room temperature (25° C.) to 300° C. at a heating rate of 120° C./h. The temperature of 300° C. was subsequently held for 3 hours and the calcination temperature was then increased from 300° C. to 567° C. at a heating rate of 125° C./h. This temperature was subsequently held for 6 hours.

The multimetal oxide obtained in this way was comminuted and the particle size fraction having a particle diameter of from 0.6 to 1.2 mm was separated out by sieving as the catalytically active multimetal oxide composition I of the stoichiometry $Co_{0.95}Mo_{0.95}W_{0.05}O_x$.

b) Preparation of a Multimetal Oxide Composition II

The preparation of the multimetal oxide composition II was carried out as in Example 1b).

c) Gas-phase Catalytic Oxidation of Propane

A reaction tube (V2A steel; 2.5 cm wall thickness; 8.5 mm internal diameter; electrically heated) having a length of 1.4 m was charged, from the bottom upward on a catalyst base (7 cm length), first to a length of 18 cm with quartz granules (number average particle diameter from 1 to 2 mm) and subsequently to a length of 42.5 cm with the active multimetal oxide composition II and then to a length of 42.5 cm with the active multimetal oxide composition I, before the charge was completed to a length of 30 cm with quartz granules (number average particle diameter from 1 to 2 mm).

The reaction tube charged as described above was heated to 395° C. over its entire length and then supplied, from the top downward, with 98 standard l/h of a reaction gas starting mixture consisting of 80% by volume of propane and 20% by volume of oxygen. The pressure at the inlet of the reaction tube was 2.69 bar (absolute). The pressure drop along the reaction tube was 0.36 bar.

In a single pass, a product gas mixture having the following characteristics was obtained:

propane conversion: 8.2 mol % selectivity of acrolein formation: 67 mol % selectivity of acrylic acid formation: 11 mol % selectivity of propane formation: 1 mol %

We claim:

1. A process for the heterogeneously catalyzed gas-phase oxidation of propane to acrolein and/or acrylic acid, in which a reaction gas starting mixture comprising propane, molecular oxygen and, if desired, inert gas is passed at from 300 to 500° C. over a fixed-bed catalyst which comprises two catalyst beds A and B arranged spatially in succession, with the proviso that the active composition of bed A is at least one multimetal oxide of the formula I $$M^1_a Mo_{1-b} M^2_b O_x \qquad (I),$$

where $M^1$=Co, Ni, Mg, Zn, Mn and/or Cu, $M^2$=W, V, Te, Nb, P, Cr, Fe, Sb, Ce, Sn and/or La, a=0.5–1.5, b=0–0.5 x=a number which is determined by the valence and amount of the elements different from oxygen in I, and the active composition of bed B is at least one multimetal oxide of the formula II

where $X^1$=W, V and/or Te, $X^2$=alkaline earth metal, Co, Ni, Zn, Mn, Cu, Cd, Sn and/or Hg, $X^3$=Fe, Cr and/or Ce, $X^4$=P, As, Sb and/or B, $X^5$=alkali metal, Tl and/or Sn, $X^6$=rare earth metal, Ti, Zr, Nb, Ta, Re, Ru, Rh, Ag, Au, Al, Ga, In, Si, Ge, Th and/or U, a'=0.01–8, b'=0.1–30, c'=0–20, d'=0–20, e'=0–20, f'=0–6, g'=0–4, h'=0–15, x'=a number which is determined by the valence and amount of the elements different from oxygen in II, wherein the reaction gas starting mixture comprises ≧50% by volume of propane, ≧15% by volume of $O_2$ and from 0 to 35% by volume of inert gas and flows through the catalyst beds A and B in the order first A, then B.

2. A process as claimed in claim 1, wherein the temperature is from 325 to 450° C.

3. A process as claimed in claim 1, wherein the temperature is from 350 to 420° C.

4. A process as claimed in claim 1, wherein the reaction gas starting mixture comprises ≧60% by volume of propane.

5. A process as claimed in claim 1, wherein the reaction gas starting mixture comprises ≧70% by volume of propane.

6. A process as claimed in claim 1, wherein the reaction gas starting mixture comprises ≧20% by volume of $O_2$.

7. A process as claimed in claim 1 which is carried out continuously.

8. A process as claimed in claim 1, wherein the molar ratio of propane to molecular oxygen in the reaction gas starting mixture is <5.

9. A process as claimed in claim 1, wherein the ratio of the bed volumes of the two catalyst beds A, B is from 1:5 to 5:1.

10. A process as claimed in claim 1, wherein the reaction pressure is >1 bar.

11. The process of claim 1, wherein $M^1$ is Co, Ni, and/or Mg and $M^2$ is Sn, W, P, Sb, and/or Cr.

12. The process of claim 1, wherein $M^1$ is Co and/or Ni and $M^2$ is W, Sn, and/or Sb.

13. The process of claim 1, wherein $X^1$ is W, $X^2$ is Co, Ni, and/or Zn, $X^3$ is Fe, $X^4$ is P and/or Sb, $X^5$ is K and/or Na.

14. The process of claim 1, wherein $X^6$ is Si, Zr, Al, Nb, Ag, and/or Ti.

15. The process of claim 1, wherein $X^6$ is Si.

16. The process of claim 1, wherein e' is 0.5–10.

17. The process of claim 1, wherein $X^6$ is Si and e' is 0.5–10.

* * * * *